(12) United States Patent
Lee et al.

(10) Patent No.: US 6,743,228 B2
(45) Date of Patent: Jun. 1, 2004

(54) DEVICES AND METHODS FOR TISSUE SEVERING AND REMOVAL

(75) Inventors: Roberta Lee, Redwood City, CA (US); Jacob Ho Huddee, San Jose, CA (US)

(73) Assignee: Manoa Medical, Inc., Redwood City, CA (US)

( * ) Notice: Subject to any disclaimer, the term of this patent is extended or adjusted under 35 U.S.C. 154(b) by 0 days.

(21) Appl. No.: 10/097,412

(22) Filed: Mar. 12, 2002

(65) Prior Publication Data

US 2003/0163129 A1 Aug. 28, 2003

Related U.S. Application Data

(60) Provisional application No. 60/322,634, filed on Sep. 12, 2001.

(51) Int. Cl.[7] .............................................. A61B 18/18
(52) U.S. Cl. ........................ 606/47; 606/113; 606/170; 606/41
(58) Field of Search .................... 606/41, 45–50, 606/110, 113, 114, 167, 170

(56) References Cited

U.S. PATENT DOCUMENTS

| | | |
|---|---|---|
| 359,506 A | 3/1887 | Goodwillie |
| 1,741,740 A | 12/1929 | Sederholm et al. |
| 1,967,015 A | 7/1934 | Wappler |
| 2,018,335 A | 10/1935 | Wappler |
| 2,047,535 A | 7/1936 | Wappler |
| 2,447,169 A | 8/1948 | Sousa |
| 2,484,059 A | 10/1949 | Wallace |
| 2,545,865 A | 3/1951 | Wallace |
| 2,729,210 A | 1/1956 | Spencer |
| 2,730,101 A | 1/1956 | Hoffman |
| 3,149,633 A | 9/1964 | Zingale |
| 3,320,957 A | 5/1967 | Sokolik |
| 3,495,586 A | 2/1970 | Regenbogen |
| 3,516,412 A | 6/1970 | Ackerman |
| 3,732,858 A | 5/1973 | Banko |
| 3,805,791 A | 4/1974 | Seuberth et al. |
| 3,815,604 A | 6/1974 | O'Malley et al. |
| 3,903,892 A | 9/1975 | Komiya |
| 3,910,279 A | 10/1975 | Okada et al. |
| 3,942,530 A | 3/1976 | Northeved |

(List continued on next page.)

FOREIGN PATENT DOCUMENTS

| | | |
|---|---|---|
| DE | 0227501 | 3/1910 |
| DE | 36 09 325 A | 9/1987 |
| DE | 39 20 707 A | 1/1991 |
| EP | 0858774 | 8/1998 |
| WO | 99/04704 | 2/1999 |
| WO | 00/30531 | 6/2000 |
| WO | WO 00 30531 A | 6/2000 |
| WO | 00/33105 | 6/2000 |
| WO | 00/76555 | 12/2000 |
| WO | 00/78221 | 12/2000 |

*Primary Examiner*—Michael Peffley
(74) *Attorney, Agent, or Firm*—Jung-hua Kuo

(57) ABSTRACT

The present invention relates to devices and methods that enhance the accuracy of lesion excision, through severing, capturing and removal of a lesion within soft tissue. Furthermore, the present invention relates to devices and methods for the excision of breast tissue based on the internal anatomy of the breast gland. A tissue severing device generally comprises a guide having at least one lumen and a cutting tool contained within the lumen. The cutting tool is capable of extending from the lumen and forming an adjustable cutting loop. The cutting loop may be widened or narrowed and the angle between the loop extension axis and the guide axis may be varied. Optional tissue marker and tissue collector may additionally be provided. A method for excising a mass of tissue from a patient is also provided. The device and method are particularly useful for excising a lesion from a human breast, e.g., through the excision and removal of a part of a breast lobe, an entire breast lobe or a breast lobe plus surrounding adjacent tissue.

64 Claims, 14 Drawing Sheets

U.S. PATENT DOCUMENTS

| | | | |
|---|---|---|---|
| 3,955,578 A | 5/1976 | Chamness |
| 4,116,198 A | 9/1978 | Roos |
| 4,181,131 A | 1/1980 | Ogiu |
| 4,294,254 A | 10/1981 | Chamness |
| 4,325,374 A | 4/1982 | Komiya |
| 4,326,530 A | 4/1982 | Fleury |
| 4,503,855 A | 3/1985 | Maslanka |
| 4,538,611 A | 9/1985 | Kelman |
| 4,718,419 A | 1/1988 | Okada |
| 4,724,836 A | 2/1988 | Okada |
| 4,732,150 A | 3/1988 | Keener Jr. |
| 4,903,696 A | 2/1990 | Stasz et al. |
| 5,003,979 A | 4/1991 | Merickel et al. |
| 5,078,716 A | 1/1992 | Doll |
| 5,083,570 A | 1/1992 | Mosby |
| 5,133,360 A | 7/1992 | Spears |
| 5,152,293 A | 10/1992 | Vonesh |
| 5,163,938 A | 11/1992 | Kambara et al. |
| 5,171,314 A | 12/1992 | Dulebohn |
| 5,196,011 A | 3/1993 | Korth et al. |
| 5,197,484 A | 3/1993 | Kornberg et al. |
| 5,201,732 A | 4/1993 | Parins |
| 5,201,741 A | 4/1993 | Dulebohn |
| 5,217,479 A | 6/1993 | Shuler |
| 5,224,488 A | 7/1993 | Neuffer |
| 5,224,945 A | 7/1993 | Pannek |
| 5,318,564 A | 6/1994 | Eggers |
| 5,323,768 A | 6/1994 | Saito et al. |
| 5,353,804 A | 10/1994 | Kornberg |
| 5,415,656 A | 5/1995 | Tihon et al. |
| 5,423,830 A | 6/1995 | Schneebaum et al. |
| 5,437,665 A | 8/1995 | Munro |
| 5,441,510 A | 8/1995 | Simpson et al. |
| 5,486,173 A | 1/1996 | Vancaillie |
| 5,569,244 A | 10/1996 | Hahnen |
| 5,630,426 A | 5/1997 | Eggers et al. |
| 5,672,172 A | 9/1997 | Zupkas |
| 5,681,324 A | 10/1997 | Kammerer et al. |
| 5,709,206 A | 1/1998 | Teboul |
| 5,709,697 A | 1/1998 | Ratcliff et al. |
| 5,733,283 A | 3/1998 | Malis et al. |
| 5,795,308 A | 8/1998 | Russin |
| 5,807,276 A | 9/1998 | Russin |
| 5,810,806 A | 9/1998 | Ritchart |
| 5,895,399 A | 4/1999 | Barbut et al. |
| 5,906,622 A * | 5/1999 | Lippitt et al. ............... 606/127 |
| 5,919,190 A | 7/1999 | VanDusseldorp |
| 5,924,175 A | 7/1999 | Lippitt et al. |
| 5,967,984 A | 10/1999 | Chu et al. |
| 5,971,994 A | 10/1999 | Fritzsch |
| 6,007,546 A | 12/1999 | Snow et al. |
| 6,015,415 A | 1/2000 | Avellanet |
| 6,022,362 A | 2/2000 | Lee et al. |
| 6,036,698 A | 3/2000 | Fawzi et al. |
| 6,063,077 A | 5/2000 | Schaer |
| 6,068,603 A | 5/2000 | Suzuki |
| 6,071,274 A | 6/2000 | Thompson et al. |
| 6,080,114 A | 6/2000 | Russin |
| 6,132,428 A | 10/2000 | VanDusseldorp |
| 6,237,605 B1 * | 5/2001 | Vaska et al. ............... 128/898 |
| 6,267,759 B1 | 7/2001 | Quick |
| 6,331,166 B1 | 12/2001 | Burbank et al. |
| 6,527,769 B2 * | 3/2003 | Langberg et al. ............. 606/41 |

\* cited by examiner

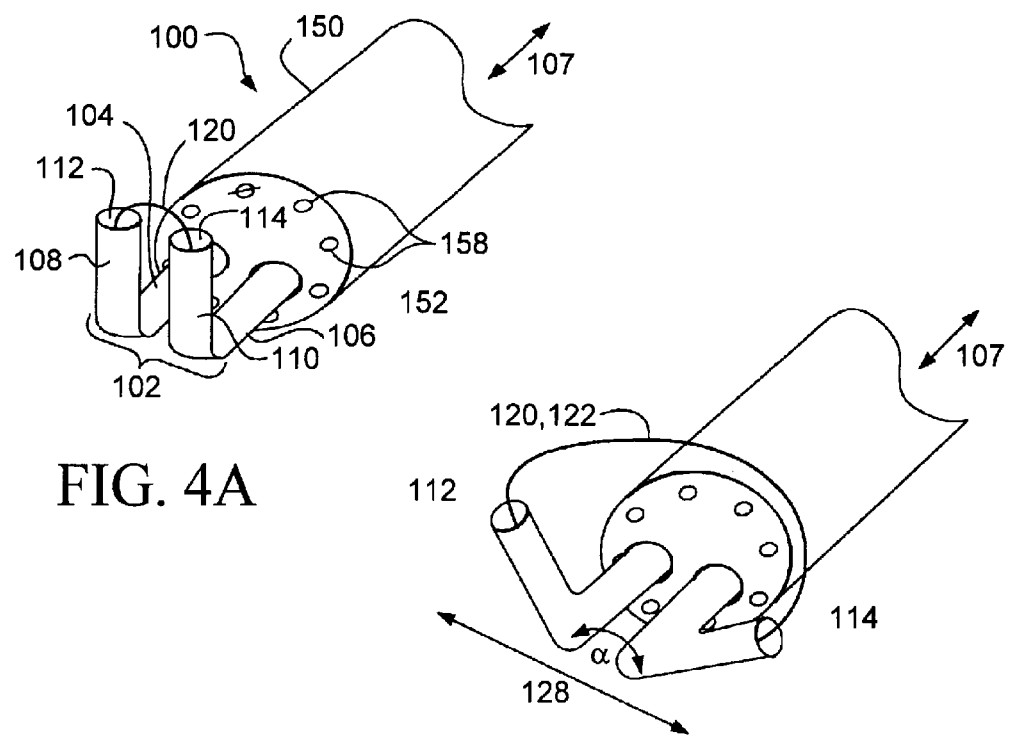
FIG. 4A
FIG. 4B
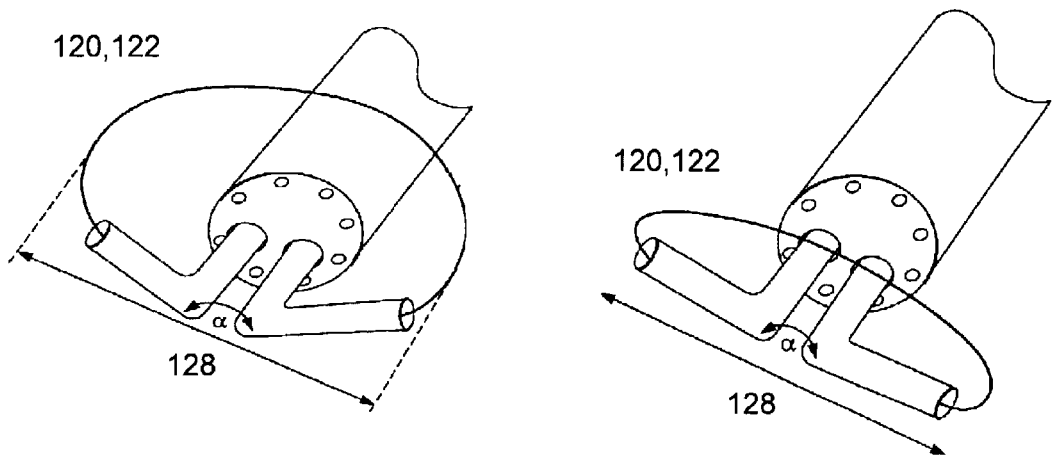
FIG. 4C
FIG. 4D

DEVICES AND METHODS FOR TISSUE SEVERING AND REMOVAL

CROSS REFERENCE TO RELATED APPLICATIONS

This application claims priority to U.S. Provisional Patent Application Serial No. 60/322,634, entitled "Tissue Severing and Removal Devices and Methods," filed on Sep. 12, 2001 which is incorporated herein by reference in its entirety.

BACKGROUND OF THE INVENTION

1. Field of the Invention

The present invention relates generally to devices and methods for severing soft tissue. In particular, the present invention relates to devices and methods that enhance the accuracy of lesion excision, through severing, capturing and removal of a lesion within soft tissue. Furthermore, the present invention relates to devices and methods for the excision of breast tissue based on the internal anatomy of the breast gland.

2. Description of Related Art

Surgery plays an important role in the diagnosis and treatment of cancer. In the case of breast cancer, surgery comprises a critical component of medical care where early diagnosis and treatment have demonstrated a significant improvement in survival.

Currently the surgical treatment of a breast cancer does not consider anatomical boundaries within the breast tissue. Anatomical boundaries are, however, important in considering the mechanism of cancer spread within the breast. The breast consists of 15 to 20 lobes that begin centrally beneath the nipple-areolar complex and extend in a radial pattern to the periphery of the gland. Milk is produced in numerous small lobules that connect to one or more main ducts within the lobe. Breast cancer begins in the epithelial cells that line the smaller branching ducts entering the lobules. The cancerous cells may multiply and spread within the ducts of the involved lobe and/or may multiply and form a defined mass. Cancerous spread within the ducts is not appreciated by mammography unless microcalcifications are present. Extension within the ducts may also be missed on pathological examination of the specimen unless a sample is taken exactly at the level of the involved duct. Using current methods of lumpectomy and examination of the specimen, these limitations may lead to inadequate surgical treatment of the cancer.

An ultrasound examination of the internal breast anatomy as described in U.S. Pat. No. 5,709,206 to Teboul, can be utilized to study the lesion and its relation to the lobe in which it is developed. By using axial ductal ultrasound scanning, identification of the affected lobe, lesion size, position within the lobe, and the possibility of other lesions within the affected lobe (e.g. multifocal cancer), and/or spread within the ducts can be delineated prior to surgical treatment.

A number of patents and publications describe excisional devices designed to remove lesions particularly from within the breast. For example, U.S. Pat. No. 6,022,362 to Lee et al. describes an excisional biopsy device for breast tissue, the device employing a tubular member having a window. A portion of the cutting tool is configured to selectively bow out of and to retract within the window. In operation, the biopsy device is inserted into soft tissue and rotated while the cutting tool is selectively bowed away from the tubular member thus severing tissue for biopsy. A tissue collection bag that is externally affixed to the tubular member may be employed to collect the severed tissue. The window is of fixed length thereby limiting the size of the excised specimen. This limits the size of lesions that can be effectively excised as a single specimen and, in addition, an entire lobe of the breast cannot be excised using this device.

U.S. Pat. No. 6,267,759 to Quick describes a cutting loop attached to a rotatable shaft. The cutting loop energized by radio frequency energy may be fashioned to form different shapes, however, there is no mechanism to adjust the size of the cutting loop. This limits the size of lesions that can be effectively excised as a single specimen and does not allow this device to excise an entire lobe.

U.S. Pat. No. 6,331,166 B1 to Burbank et al. describes a tissue acquisition system that includes radio frequency cutter loops which are extendible out of a cannula to cut cylindrical tissue samples. The cutter loops are also of fixed diameter thereby limiting the size of the lesion that can be excised as a single specimen and does not allow the device to excise an entire lobe.

Accordingly, there is a need for a surgical excisional device that can accurately excise a lesion as a single tissue specimen, that can adapt to lesions of different sizes by varying the size of the cutting mechanism, and that can capture and remove the specimen through a small incision. The device should minimize scarring to the remaining breast tissue by including within the specimen only the necessary amount of surrounding normal breast tissue required to obtain adequate margins. The method of severing and retrieving the sample of tissue should be performed in a manner that minimizes the risk of cancer cell dissemination. Further, there is a need for a therapeutic surgical device and/or method of treatment of breast cancer, that accurately excises part of a lobe, an entire lobe or more than an entire lobe as a single specimen.

SUMMARY OF THE INVENTION

The present invention relates to devices and methods that enhance the accuracy of lesion excision, through severing, capturing and removal of a lesion within soft tissue. Furthermore, the present invention relates to devices and methods for the excision of breast tissue based on the internal anatomy of the breast gland. It should be appreciated that the present invention can be implemented in numerous ways, including as a process, an apparatus, a system, a device, or a method. Several inventive embodiments of the present invention are described below.

The devices and methods described herein are preferably adapted to accurately and safely excise a mass of tissue from the breast or other soft tissue as a single specimen and with minimal invasiveness. The amount of tissue excised is variable and preferably not limited by the mechanism of the device. Further, the devices and methods improve the accuracy of positioning the device with respect to the lesion.

The devices and methods facilitate safe capture and removal of the severed tissue from the body to minimize potential cancer cell dissemination. Moreover, the devices and methods are adapted to accurately and safely excise part of a lobe of a breast, the entire lobe or more than the entire lobe for therapeutic surgical treatment of breast cancer. Optionally, the devices and methods provide for marking or labeling the specimen in vivo to enable specimen orientation once removed from the body.

According to a preferred embodiment, a tissue severing device generally comprises a guide, a cutting tool contained within the guide and capable of forming a cutting loop extending from the guide and having a loop extension axis defined by the direction in which the cutting loop extends, and an extension means for controlling the degree to which the cutting loop extends from the guide. The guide comprises two co-linear, co-extensive guide lumens longitudinally extending from a proximal region to a distal terminus along a guide axis and the guide lumens have co-extensive distal segments terminating in distal tips from which the cutting loop extends. The angle of each distal segment in relation to the guide axis is generally fixed.

The distal tips may be at a generally fixed distance therebetween such that the width of the cutting loop when the cutting loop is extended is generally fixed. Alternatively, the device may further comprise a width adjuster for selectively moving the distal tips of the distal segments relative to each other to thereby selectively adjust the width of the cutting loop. The width adjuster varies the distance between the distal tips by rotating at least one of the guide lumens.

According to another preferred embodiment, a tissue severing device generally comprises a guide, a cutting tool contained within the guide and capable of forming a cutting loop having a loop extension axis defined by the direction in which the cutting loop extends, an extension means for controlling the degree to which the cutting loop extends from the guide, and a distal segment positioning means for varying the direction of each distal segment with respect to the guide axis to thereby adjust the angle between the loop extension axis and the guide axis and selectively position the cutting loop with respect to the guide axis. The guide comprises two co-linear, co-extensive guide lumens longitudinally extending from a proximal region to a distal terminus along a guide axis and the guide lumens have co-extensive distal segments terminating in distal tips from which the cutting loop extends and deformable regions immediately proximal to the distal segments. The deformable regions facilitate in changing the direction of the distal segments with respect to the guide axis.

The distal segment positioning means may comprise retraction cables, each attached to one of the distal segments such that selective tightening and relaxing of the retraction cables adjusts the direction of the distal segments with respect to the guide axis. In addition, selective tightening and relaxing of the retraction cables may further position the cutting loop when extended so as to adjust the angle between the loop extension axis and the guide axis to thereby reposition the cutting loop with respect to the guide axis. The retraction cables may be at least partially and movably disposed within said guide lumens. In an alternative, the deformable regions may comprise a shape-memory material.

The distal tips may be at a generally fixed distance therebetween such that the width of the cutting loop when the cutting loop is extended is generally fixed. Alternatively, the device may further comprise a width adjuster to facilitate in selectively moving the distal tips of the distal segments relative to each other to thereby selectively adjust the width of the cutting loop. The width adjuster moves the distal tips of the distal segments and varies the distance between the distal tips by rotating at least one of the guide lumens.

According to yet another preferred embodiment, a tissue severing device generally comprises a guide comprising a guide lumen, a cutting tool having a fixed end and is at least partially contained within the guide lumen when in a stored configuration and extendible from a distal tip thereof, an extension means for controlling the degree to which the cutting loop extends from the guide lumen, and a width adjuster for selectively adjusting the width of the cutting loop. The guide lumen longitudinally extends from a proximal region to a distal terminus along a guide axis and has a distal segment terminating in the distal tip. Extension of the cutting tool from the guide lumen forms a cutting loop having a loop extension axis defined by the direction in which the cutting loop extends.

According to a preferred embodiment, a method for excising a lobe from within a human patient's breast generally comprises locating the lobe to be excised within the breast and excising at least a part of the lobe utilizing a tissue severing device. The method may further comprise locating a lesion within a lobe of the breast, evaluating the size of the lesion, identifying any extensions of the lesion and any additional lesions within the lobe, and determining from the locating, evaluating, and identifying whether to excise at least a part of the lobe, the entire lobe or the entire lobe plus additional surrounding tissue in the excising in order to remove the lesion or lesions from the breast.

The identifying step may generally comprise identifying any extensions of the lesion within the duct system and evaluating the lobe of the breast for additional lesions. Moreover, at least one of the locating, evaluating, identifying, and employing may be carried out using a radiological imaging modality such as ultrasound imaging or magnetic resonance imaging (MRI).

According to another preferred embodiment, a method for removing a lesion from a patient generally comprises locating the lesion to be severed and removed from within a selected region of the patient, inserting a guide through an incision, advancing the guide into the selected region, extending a cutting tool contained within the guide from the distal tips of the two guide lumens to form a cutting loop having a loop extension axis defined by the direction in which the cutting loop extends, and moving the cutting loop using the guide along the guide axis to sever tissue containing the lesion from the selected region.

The guide advanced by the method generally comprises two co-linear, co-extensive guide lumens longitudinally extending from a proximal region to a distal terminus along a guide axis and having co-extensive distal segments terminating in distal tips. In one embodiment, the angle of each distal segment relative to the guide axis is generally fixed.

Alternatively, the guide lumens of the guide advanced by the method have deformable regions immediately proximal to the distal segments that facilitate in changing the direction of each distal segment with respect to the guide axis. The method may further comprise varying the direction of at least one of the distal segments with respect to the guide axis, thereby changing the angle between the loop extension axis and the guide axis, whereby the cutting loop is repositioned with respect to the guide axis. The distal segments of the guide lumens may optionally maintain a generally fixed distance therebetween. Alternatively, the method may further comprise, prior to or during the extending, varying the distance between the distal segments to selectively widen or narrow the cutting loop.

According to yet another preferred embodiment, the guide advanced by the method comprises a guide lumen longitudinally extending from a proximal region to a distal terminus along a guide axis, the guide lumen has a distal segment terminating in a distal tip and the cutting tool has a fixed end at least partially contained within the guide lumen when in a stored configuration and is extendable from the distal tip thereof to form a cutting loop.

These and other features and advantages of the present invention will be presented in more detail in the following detailed description and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which:

FIGS. 4A–4D, collectively referred to as FIG. 4, illustrate a mechanism for varying the width of a cutting loop by rotating the guide lumens around a guide axis and with respect to each other;

DESCRIPTION OF SPECIFIC EMBODIMENTS

Figure 1A:
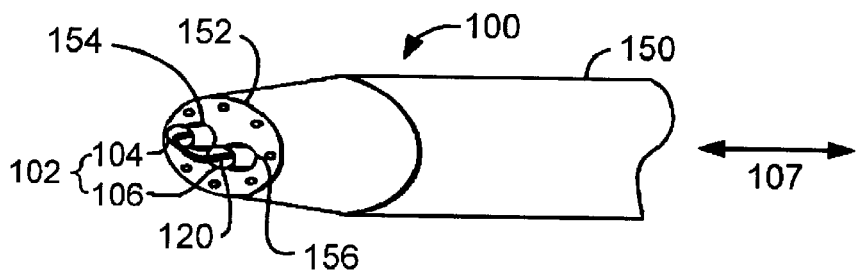
FIGS. 1A–1E, collectively referred to as FIG. 1, illustrate a version of the device that employs a cutting tool contained in a guide having two guide lumens in which the guide is housed in a tubular shaft and is adapted to extend out of and retract into the distal end of the tubular shaft.

The present invention relates to devices and methods that enhance the accuracy of lesion excision, through severing, capturing and removal of a lesion within soft tissue. Furthermore, the present invention relates to devices and methods for the excision of breast tissue based on the internal anatomy of the breast gland. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

The present invention relates to tissue severing and removal devices as well as methods for severing and removing tissue. While the invention is generally useful for procedures in soft tissue, the devices are particularly effective in providing precise control during the excision of a lesion or abnormality in breast tissue with minimal invasiveness. In particular a method for severing and removal of part of a lobe, an entire lobe or an entire lobe plus surrounding tissue within a breast is described.

FIG. 1 illustrates the distal region of an embodiment of a tissue severing device 100. As is the case with all figures herein, FIG. 1 is not to scale and certain dimensions may be exaggerated for clarity of presentation. As shown, the device 100 includes a guide 102 comprising two co-linear, co-extensive guide lumens 104, 106. The guide lumens 104, 106 extend longitudinally from a proximal region (not shown) to a distal end 152 along a guide axis 107, an imaginary line that lies along the longest dimension of the guide 102. The guide lumens 104, 106 have co-extensive distal segments 108, 110 terminating in distal tips 112, 114. Each distal segment 108, 110 has a deformable region 116, 118 located in a proximal region of the corresponding distal segment 108, 110, respectively. The deformable regions 116, 118 enable each distal segment 108, 110 to change direction with respect to the guide axis 107. As shown, each distal segment 108, 110 and the corresponding deformable regions 116, 118, respectively, are preferably formed as a single piece. That is, the entirety of each distal segment 108, 110 is formed from a deformable material. Alternatively, each distal segment 108, 110 may be formed from integrating or joining separate components comprising one or more materials.

As shown in FIG. 1, the guide 102 containing guide lumens 104, 106 is housed in a tubular shaft 150. Located at a distal end 152 of the tubular shaft 150 are two openings 154, 156 that allow the guide lumens 104, 106, respectively, to extend from and retract into the tubular shaft 150. Any suitable mechanism (not shown) may be provided for controlling the degree to which the guide lumens 104, 106 are extended from or retracted into the tubular shaft 150. In FIG. 1A, the guide lumens 104, 106 are in a retracted position such that a substantial portion of the distal segments 108, 110 are contained within the tubular shaft 150. This arrangement of the guide 102 and the tubular shaft 150 allows an exposed cutting tool 120 to aid in tissue penetration. FIG. 1B illustrates the extension of the guide lumens 104, 106 in direction 109 until at least the deformable regions 116, 118 are external to the tubular shaft 150.

The tubular shaft 150 and the guide 102 are typically sufficiently rigid such that the act of penetrating the device 100 into tissue will not cause bending or deflection of either the tubular shaft 150 or the guide 102. Generally either or both the tubular shaft 150 and the guide 102 may be constructed from a metallic material such as stainless steel. However, ceramic materials such as alumina and silica or rigid plastic materials such as polystyrene and polyester and/or any other suitable material may also be employed. In addition, the interior and/or exterior surfaces of the tubular shaft 150 and the guide 102 may be coated with a low friction material such as Teflon®, polyvinylidene fluoride, polyethylene, or another polymeric material to facilitate penetration of tissue by the tubular shaft 150 and the guide 102, facilitate movement of the guide lumens 104, 106 with respect to the tubular shaft 150, and/or facilitate movement of the cutting tool 120 within the guide lumens 104, 106.

Further, the tubular shaft 150 may include one or more accessory lumens. Such accessory lumens typically extend from lumen openings 158 located at or near the distal end 152 of the tubular shaft 150, as illustrated in FIGS. 1 and 4. An accessory lumen may comprise a transport lumen that allows a material to be transported therethrough to the distal end 152. Gas, liquid, or a combination thereof from an external source may be administered through the transport lumen to the distal end 152. For example, an aqueous solution may be employed for irrigation purposes or a local anesthetic, such as lidocaine, may be administered through the transport lumen. In addition, one or more of the accessory lumens may be operatively connected to an external vacuum source. The external vacuum source may provide suction to remove from the patient, fluids such as blood, irrigation fluid or smoke generated during use of the cutting tool 120. It should be noted that for versions of the device 100 that do not include the tubular shaft 150, the guide 102 may be constructed to conform to the preferred characteristics of the tubular shaft 150.

Another embodiment of the guide 102 housed in the tubular shaft 150 is illustrated in FIG. 2. The distal end 152 of the tubular shaft 150 contains a tissue penetrant 162 that facilitates advancement of the device 100 into tissue. The tissue penetrant 162 may be configured to a sharp point (as shown in FIG. 2), a trocar, a scalpel-like blade, or any other suitable mechanism. Additionally or alternatively, the tissue penetrant 162 may be operatively connected to an external energy source (not shown). While the external energy source may employ thermal, ultrasonic, or any other suitable energy, the energy source is preferably a radio frequency energy source. Using a radio frequency energy source, the tissue penetrant 162 may function as a component of a monopolar or a bipolar system.

A primary window 160 is located near the distal end 152 of the tubular shaft 150. The distal tips 112, 114 are aligned with the primary window 160. The direction of the distal segments 108, 110 with respect to the guide axis 107 may be predetermined or may be varied as illustrated in FIG. 1. As shown in FIG. 2D, a window cover 166 may be used to cover and uncover the primary window 160. During tissue penetration, it is advantageous to prevent tissue from becoming entrapped in the primary window 160 as this may interfere with the function of the guide 102 or of the cutting tool 120. The window cover 166 may initially cover the primary window 160 to create a smooth, tapered shape to the tubular shaft 150 during tissue penetration. Prior to extension of the cutting tool 120 to create a cutting loop (not shown), a window controller (not shown) may be used to slide the window cover 166 in the proximal direction 168 to expose the primary window 160 and the cutting tool 120 to the tissue. Similarly, the window cover 166 may slide back to its original position to cover the primary window 160.

Figure 1B:
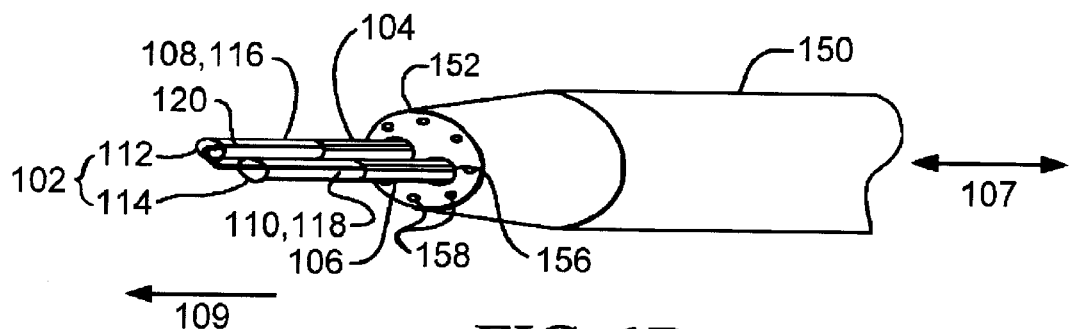
Figure 1C:
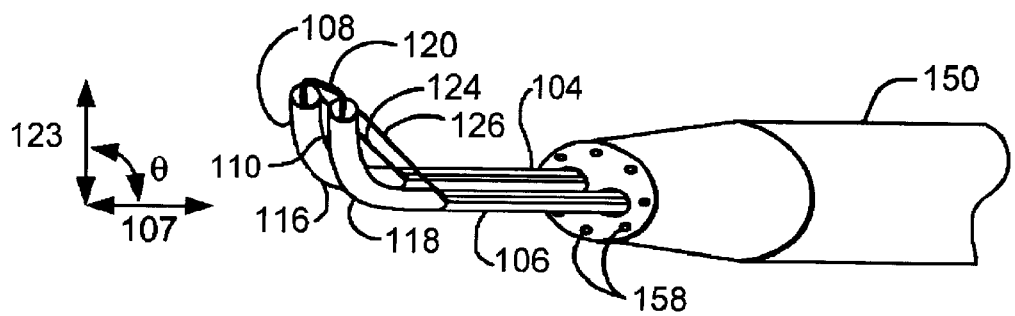
Figure 1D:
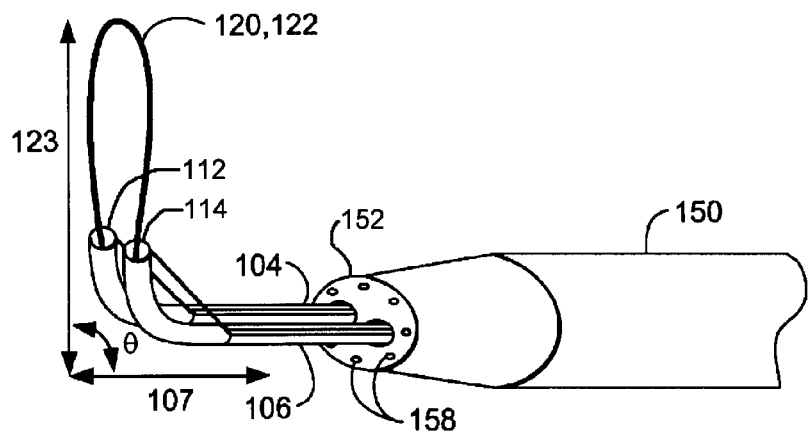
Figure 2A:
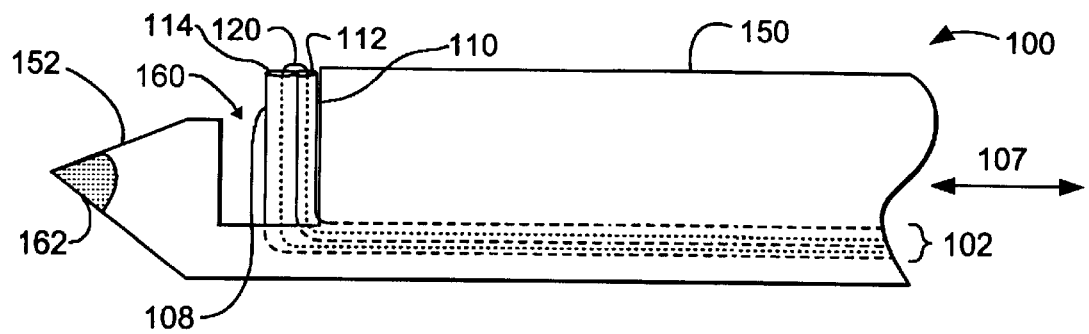
FIGS. 2A–2E, collectively referred to as FIG. 2, illustrate another version of the device that employs a cutting tool contained in a guide having two guide lumens in which the guide is housed in a tubular shaft, a primary window is located near the distal end of the tubular shaft, and the distal tips of the two guide lumens are aligned with the primary window.
Figure 2B:
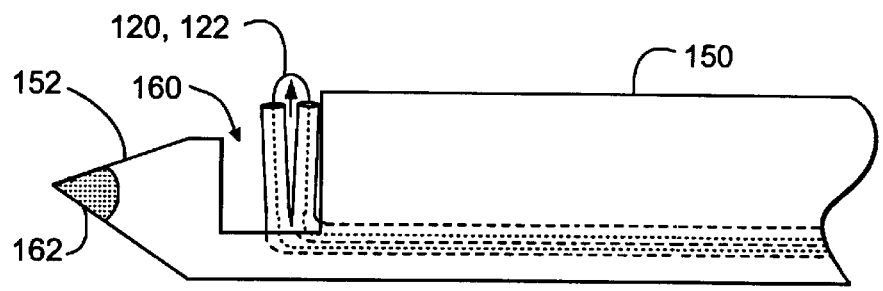
Figure 2C:
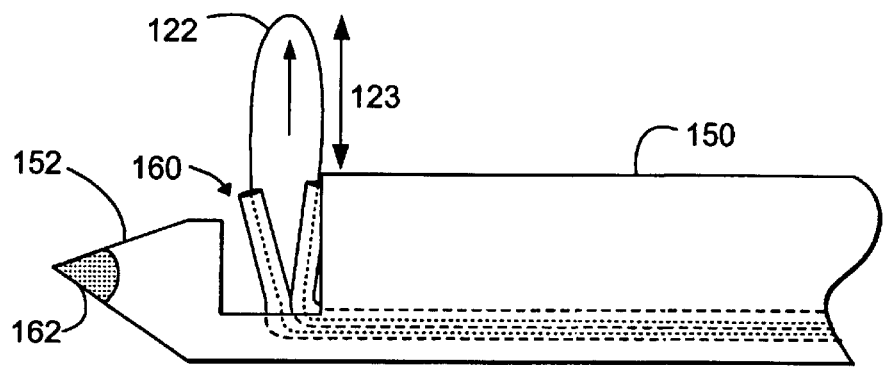
Figure 2D:
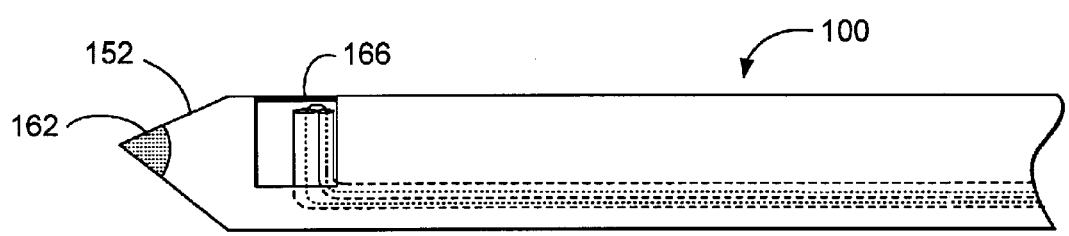
Figure 2E:
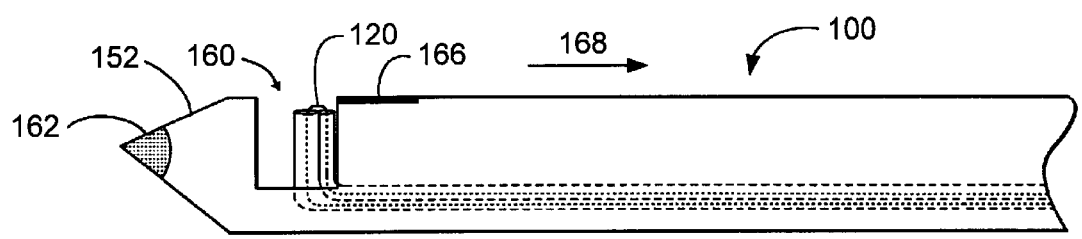

In FIG. 1B, when the guide 102 is extended out of the distal end 152 of the tubular shaft 150, the distal segments 108, 110 can move with respect to the guide axis 107. As shown in FIG. 1C, retraction cables 124, 126 are employed to change the direction of the distal segments 108, 110 with respect to the guide axis 107 such that, for example, the distal segments 108, 110 are generally in an orthogonal orientation with respect to the guide axis 107. Thus, tightening or relaxing the retraction cables 124, 126 serves to position the cutting loop 122 so as to vary the angle θ between a loop extension axis 123 and the guide axis 107, resulting in repositioning of the cutting loop 122 with respect to the guide axis 107. Alternatively, the retraction cables 124, 126 may be housed within the wall of the guide lumens 104, 106 or any other suitable control mechanism for controlling the orientation of the distal segments 108, 110 may be employed. Alternatively or additionally, the deformable regions 116, 118 may be made of a shape-memory metal or metal alloy such as a nickel-titanium alloy. With the deformable regions 116, 118 made of a shape-memory material, the deformable regions 116, 118 deform to position distal segments 108, 110 at a predetermined direction with respect to the guide axis 107 when the guide 102 is extended out of the distal end 152 of the tubular shaft 150. Thus, the cutting loop 122 can be positioned without the provision or use of retraction cables.

In any of the embodiments disclosed herein, the angle θ between the guide axis 107 and the loop extension axis 123 when the cutting loop 122 is extended may alternatively be generally fixed at a predetermined angle rather than adjustable. For example, the retraction cables 124, 126 may be replaced by elastic cables (not shown) that are not selectively retractable. Before the distal segments 108, 110 are extended out of the distal end 152 of the tubular shaft 150, the elastic cables are stretched and extended to allow the distal segments 108, 110 to generally extend along the guide axis 107. When the distal segments 108, 110 are extended out of the distal end 152 of the tubular shaft 150, the elastic cables contract to a predetermined length to position the distal segments 108, 110 such that the angle θ between the guide axis 107 and the loop extension axis 123 when the cutting loop 122 is extended is generally fixed at a predetermined angle. As another example, when the deformable regions 116, 118 are made of a shape-memory material, the direction of the distal segments 108, 110 when extended out of the distal end 152 of the tubular shaft 150, is generally fixed.

It is noted that the angles between each distal segment 108, 110 and the guide axis 107 may be either the same or different. For example, in the case where the device 100 comprises retraction cables 124, 126, the retraction cables 124, 126 may be retracted by a same or different amount so that the distal segments 108, 110 are in the same or different orientation relative to the guide axis 107.

FIG. 4 illustrates a cutting loop adjuster for adjusting the width of the cutting loop 122. In FIG. 4A, the distal segments 108, 110 are in an orthogonal orientation with respect to the guide axis 107. FIGS. 4B, 4C and 4D demonstrate that by rotating one or both of the guide lumens 104, 106 around the guide axis 107 such that the distal tips 112, 114 move away from each other, the cutting loop width 128 progressively increases in size until a maximal cutting loop width 128 is achieved when the distal tips 112, 114 are facing opposite directions or an angle a is 180°.

It is noted that although a cutting loop 122 with an adjustable width may be provided, a generally fixed cutting loop width 128 may alternatively be provided in any of the embodiments disclosed herein. For example, the distal tips 112, 114 may be at a generally fixed distance relative to each other such that the cutting loop width 128 is generally fixed. A generally fixed cutting loop width 128 may be provided where, for example, the guide lumens 104, 106 are generally not rotatable about the guide axis 107 such that the distal tips 112, 114 remain in a fixed distance relative to each other. It is further noted that where the cutting loop width 128 is generally fixed, the cutting loop 122 may nonetheless be extended and/or retracted as appropriate to a desired extension or loop size.

Figure 3:
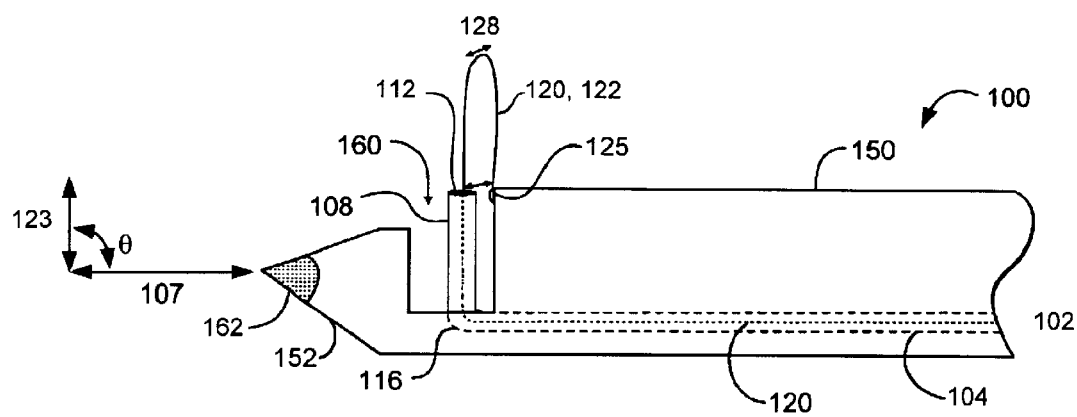
FIG. 3 illustrates another embodiment of the tissue severing device in which the guide comprises a single guide lumen and the cutting tool is housed within a tubular shaft, has a fixed end, is at least partially contained within the guide lumen, and is extendible through a primary window near the distal end of the tubular shaft.

FIG. 3 illustrates another embodiment in which a tissue severing device is similar to that described above except the guide 102 comprises the guide lumen 104 that longitudinally extends along the guide axis 107 from a proximal region (not shown) to a distal segment 108. The distal segment 108 terminates in the distal tip 112. The distal segment 108 includes the deformable region 116. The deformable region 116 may change the direction of the distal segment 108 with respect to the guide axis 107 and thus define an angle θ between the distal tip 112 and the guide axis 107. As shown in FIG. 3, the guide 102 is housed in the tubular shaft 150 similar to that shown in FIG. 2, where the tubular shaft 150 has the window 160 near the distal end 152 such that the distal tip 112 of the guide 102 is aligned with the window 160.

As illustrated in FIG. 3, the cutting tool 120 is partially contained in the guide lumen 104. The cutting tool 120 has a fixed end 125 that may be attached to an external portion of the guide 102, or in an alternative, as depicted in FIG. 3, the fixed end 125 may be attached to the tubular shaft 150. In either case, the cutting tool 120 is capable of forming the cutting loop 122 extending from the distal tip 112 of the guide lumen 104. Any suitable extension mechanism (not shown) may provide control over the degree to which the cutting loop 122 extends from the guide lumen 104. Alternatively or additionally, where the fixed end 125 is attached to the tubular shaft 150, the cutting loop width 128 can be varied by rotating the guide 102 within the tubular shaft 150 so as to vary the distance between the distal tip 112 and the fixed end 125. In one embodiment, the distance between the distal tip 112 and the fixed end 125 is generally fixed such that the cutting loop width 128 is generally fixed. It is noted that although the cutting loop width 128 is generally fixed, the cutting loop 122 may nonetheless be extended and/or retracted as appropriate to a desired extension or size.

The direction of the distal segment 108 with respect to the guide axis 107 may be varied and/or adjusted by tightening or relaxing a retraction cable (not shown) similar to that described with reference to FIG. 1. Alternatively, the direction of the distal segment 108 with respect to the guide axis 107 may be predetermined and fixed.

Each of FIGS. 1 and 2 illustrates a preferred arrangement in which at least a portion of the cutting tool 120 is disposed in each of the guide lumens 104, 106. The cutting tool 120 is capable of forming the cutting loop 122 by extending the cutting tool 120 from one or both of the distal tips 112, 114, as shown in FIG. 1D. This extension may be accomplished using any suitable extension mechanism that provides control over the degree to which the cutting loop 122 extends from the guide 102. Typically, such extension mechanism may incorporate a dial on a handle 190 as illustrated in FIG. 9 or a knob (not shown) that can be pushed or pulled along the handle in the direction of the guide axis 107, to extend and retract the cutting tool 120, respectively, or any other mechanism known to those skilled in the art.

The cutting tool 120 may be configured in one of any number of forms to facilitate the cutting or severing of soft tissue such as breast tissue. For example, the cutting tool 120 may be a wire or a thin ribbon. The cross-sectional shape of the cutting tool 120 may be round, rectangular, square, triangular or any other shape that facilitates the cutting of soft tissue. One or both edges of the cutting tool 120 may be sharpened, serrated or both. The cutting tool 120 may comprise a metallic material such as a metal, a metal alloy, a metal laminate, or a metal composite. The metallic material may be, for example, nickel, titanium, iron, cobalt, chromium, copper, tantalum, tungsten, and alloys thereof. Preferred metallic materials include titanium, a titanium alloy such as a nickel-titanium alloy, and alloys such as those typically used in stainless steel.

Figure 9:
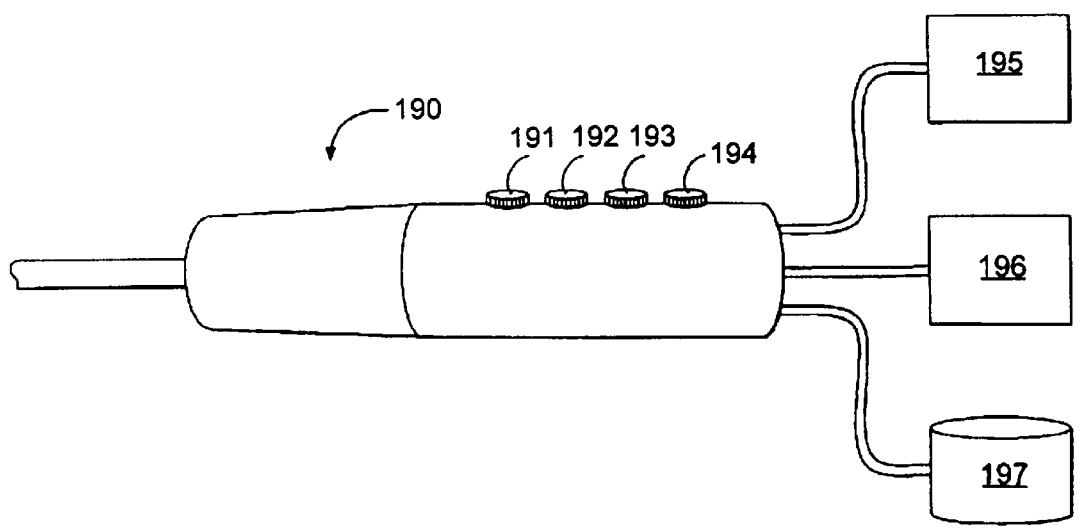
FIG. 9 illustrates a handle that may be employed with the tissue severing device described herein.

The cutting tool 120 may be operatively connected to an external energy source 195 (as shown in FIG. 9). The external energy source may be a radio frequency energy source and the cutting tool 120 comprises an electrically conductive material. The cutting tool 120 may operate as a monopolar electrode. The cutting tool 120 may also operate as a bipolar electrode with both electrodes located on the cutting tool 120, itself, or with the return electrode located elsewhere on the device 100. The cutting tool 120 may be designed to cauterize as well as cut tissue to control excessive bleeding. When electrical current is transmitted through the cutting tool 120, it is preferred that the guide lumens 104, 106 comprise an electrically insulating material or are coated with such a material to electrically isolate the cutting tool 120 within the device 100.

Additionally or alternatively, the cutting tool 120 may employ mechanical action to cut or sever tissue. For example, a vibrator may be included for inducing mechanical vibration of the cutting tool 120. As another example, the cutting tool 120 may employ an ultrasonic energy source to cut tissue. Other variations relating to cutting tool design and implementation are known to those skilled in the art.

The device 100 may further include a tissue collector for collecting and removing tissue severed by the cutting tool 120. As the device 100 may be employed to sever tissue containing a malignant tumor, the tissue collector is preferably designed to reduce the potential spread of cancerous cells. For example, the tissue collector may comprise a collection bag with an adjustable opening that provides communication to its interior. The collection bag preferably comprises an impermeable material to retain fluid and loose tissue or cells. This reduces the potential for spreading dislodged cancerous cells during removal of the collection bag from the patient. The collection bag is preferably thin-walled and supple. A number of plastic or polymeric materials may be used to construct the collection bag. These materials include, but are not limited to, polyethylene, polypropylene, polybutylene, polyamide, polyimide, polyester, polyvinyl chloride, polyvinyl fluoride, polyvinylidene fluoride, polycarbonate, and polytetrafluoroethylene.

The collection bag (not shown) may be attached to the cutting tool 120. Thus, the collection bag may open or close by increasing or decreasing the size of the cutting loop 122, respectively. As tissue is severed by the cutting loop 122, the severed tissue enters the collection bag as the collection bag follows the path of the cutting loop 122. In such a configuration, the collection bag is typically insulated from the cutting tool 120.

Figure 1E:
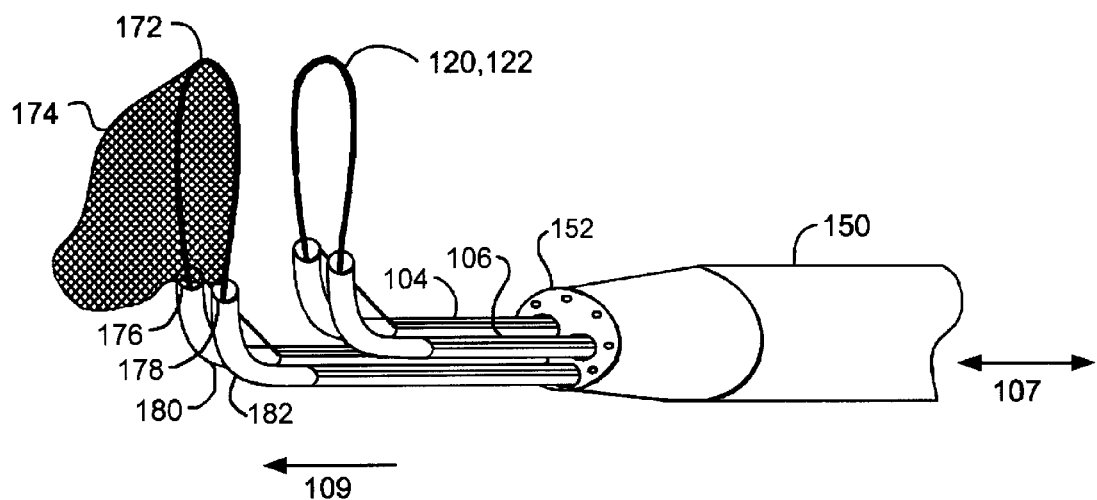
Figure 6A:
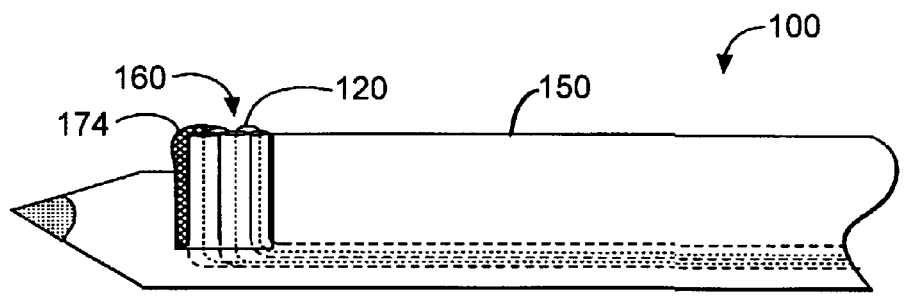
FIGS. 6A–6C illustrates another embodiment similar to that shown in FIG. 2, in which a tissue capturing mechanism is contained within the same primary window as the distal tips of the guide lumens.

Alternatively, the collection bag may be independently deployable with respect to the cutting loop 122. As illustrated in FIGS. 1E and 6, a collection bag 174 may be attached to a collection loop 172 that is controlled similar to the manner in which the cutting loop 122 is controlled. The collection loop 172 extends from collection distal tips 176, 178 of two collection lumens 180, 182. The collection loop 172 is generally orthogonal to the guide axis 107. The collection lumens 180, 182 are similar in design to the guide lumens 104, 106. As a result, the collection loop 172 may be extended, widened, narrowed, or repositioned with respect to the guide axis 107. In some instances the cutting loop adjuster may also be used to adjust the collection loop 172. Alternatively, a collection loop adjuster may be employed to control the collection loop 172 independently of the cutting loop 122. As the collection loop 172 extends from the collection distal tips 176, 178, the collection bag 174 opens allowing severed tissue to enter and as the collection loop 172 retracts, the collection bag 174 closes trapping the severed tissue within.

One or more points along the opening of the collection bag 174, e.g., adjacent the collection distal tips 176, 178, may be fixedly attached to (or adjacent to) the collection distal tip(s) 176, 178 of the collection lumen(s) 180, 182 and/or predetermined location(s) on the collection loop 172. The remainder portion along the opening of the collection bag 174 is preferably movably or slidably attached to the collection loop 172. Thus, when the collection bag 174 is in a retracted or stored configuration, the collection bag 174 may be tucked within or along the outside of one or both of the collection lumens 180, 182 and/or the tubular shaft 150 until the collection bag 174 is deployed.

Figure 5:
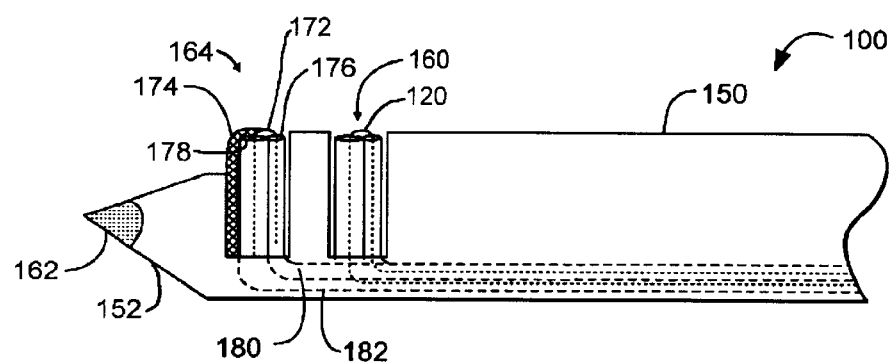
FIG. 5 illustrates another embodiment similar to that shown in FIG. 2, in which the tubular shaft comprises an additional window which contains a tissue capturing mechanism.
Figure 6B:
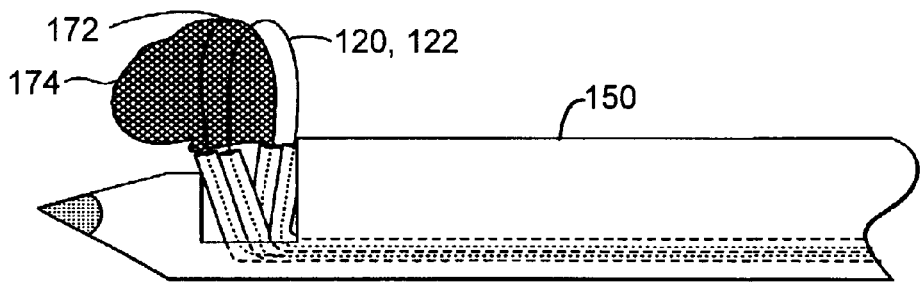
Figure 6C:
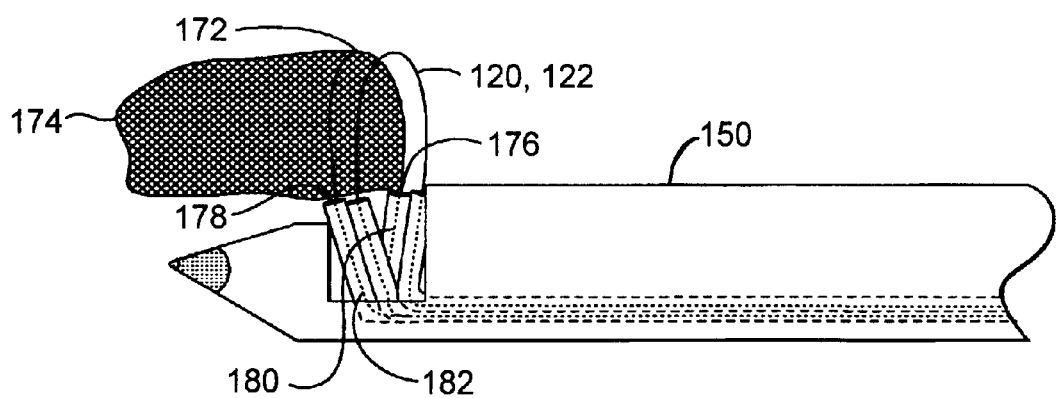
Figure 7A:
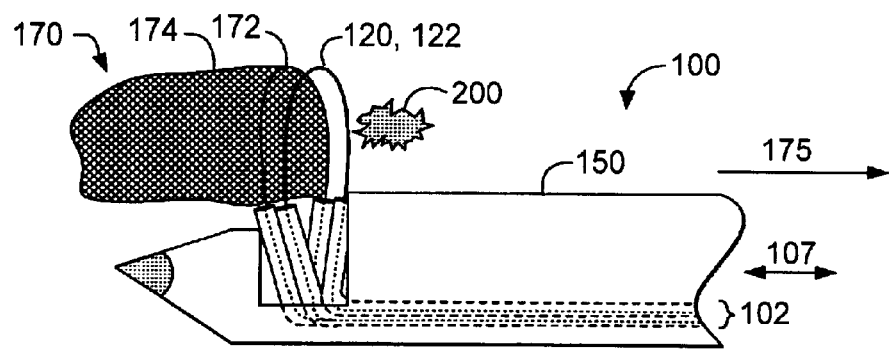
FIGS. 7A–7D, collectively referred to as FIG. 7, illustrate the operation of an embodiment similar to that shown in FIG. 6.
Figure 7B:
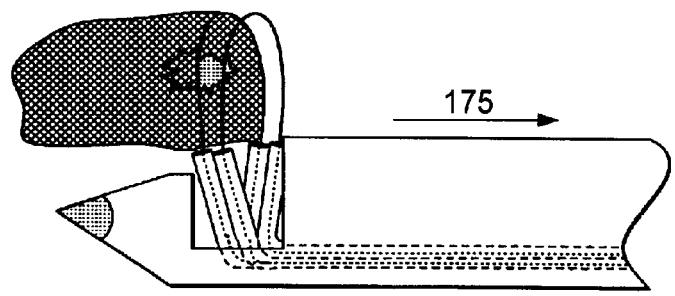
Figure 7C:
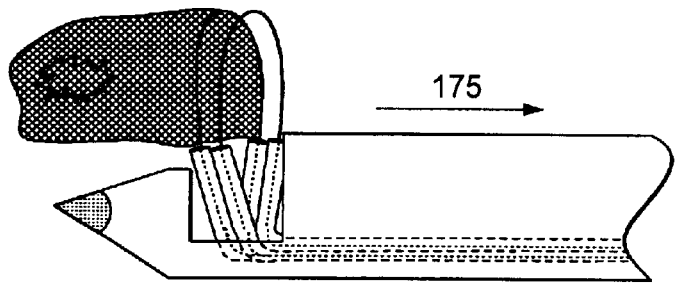
Figure 7D:
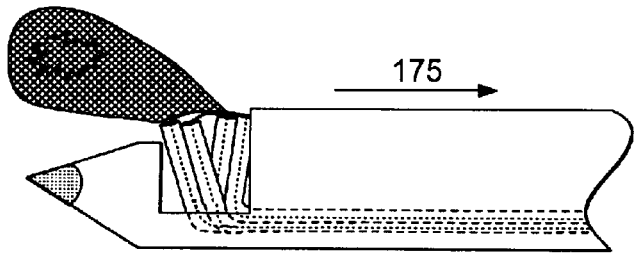

In FIG. 1E, the collection loop 172 is aligned with the cutting loop 122. The collection lumens 180, 182 extend from the distal end 152 along direction 109 similar to the guide lumens 104, 106. In the embodiment of the device 100 illustrated in FIG. 6, the collection distal tips 176, 178 are aligned with the primary window 160. The collection bag 174 is contained within the tubular shaft 150 or is contained on the external surface of the tubular shaft 150. FIGS. 6B and 6C illustrate the collection loop 172 extended from the collection distal tips 176, 178 with the collection bag 174 partially deployed as in FIG. 6B and fully deployed as in FIG. 6C. Alternatively, as shown in FIG. 5, the collection distal tips 176, 178 may be aligned with an additional window 164 near the distal end 152 of the tubular shaft 150.

FIG. 7 illustrates the device 100 in use after the cutting tool 120 has been extended to create the cutting loop 122 and the collection loop 172 has been extended to deploy the collection bag 174. As the tubular shaft 150 moves in a direction 175, along the guide axis 107, the cutting loop 122 severs the tissue around a lesion 200. The severed tissue enters the collection bag 174 as the collection bag 174 closely follows in the path created by the cutting loop 122. As a result, a mass of tissue containing the lesion 200 is severed and contained in the collection bag 174. Retraction of the collection loop 172 closes the collection bag 174, thereby capturing the lesion 200 within the mass of tissue.

The device 100 allows tissue to be severed and collected along a straight path. If the severed tissue does not rotate or change orientation with respect to the guide axis 107 as it is removed from the patient, the surgeon or operator can carefully remove the severed tissue from the collection bag 174 without disturbing the orientation of the severed tissue. The surgeon or operator may then mark the specimen with various dyes commonly used for said purpose or with sutures or clips.

According to a preferred embodiment shown in FIG. 8, the tissue severing device may further comprise a tissue marker for marking in vivo the mass of tissue severed, i.e., before it is removed from the patient. In one embodiment, a tissue marker, illustrated in FIG. 8A, comprises a series of marking segments 302, 304 and 306 attached to and/or extending from the cutting loop 122. The marking segments 302, 304 and 306 may comprise a series of thin strands of electrically conductive wires that trail behind the cutting loop 122 as tissue is severed. The marking segments 302, 304 and 306 may be in electrical communication with the cutting loop 122. If a radio frequency energy source is used to energize the cutting loop 122, the marking segments 302, 304 and 306 may be similarly energized. By contacting the cut surface of the severed tissue, the marking segments 302, 304 and 306 may cause a blackening or charring of the cut surface, thereby producing different marks on the different sides of the severed tissue. The marking segments 302, 304 and 306 may be arranged in any fashion to orient the severed tissue, one example being illustrated in FIG. 8A. The marking segments 302, 304 and 306 and the cutting tool 120 may be formed as a single component or as an alternative, the marking segments 302, 304 and 306 may be attached to the cutting tool 120. The marking segments 302, 304 and 306 may comprise a metal, a metal alloy, a metal laminate, or a metal composite. The marking segments 302, 304 and 306 may comprise a braided metal, a braided metal alloy, a braided metal laminate or a braided metal composite.

Figure 8A:
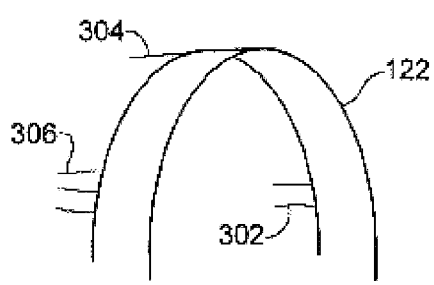
FIGS. 8A–8E, collectively referred to as FIG. 8, illustrate embodiments of a tissue marker.
Figure 8B:
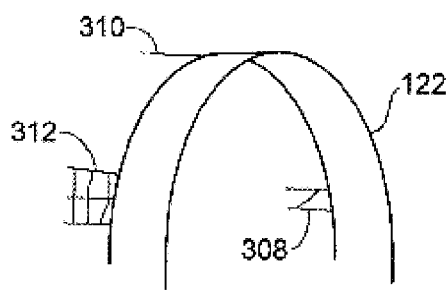

As yet a further alternative, the marking segments may be constructed into any pattern or patterns 308, 310 and 312 as illustrated in FIG. 8B. The marking segments in any of the above alternative embodiments are preferably designed not to contact or interfere with the tissue collector such as the collection bag 174 (shown in FIG. 8D).

Figure 8C:
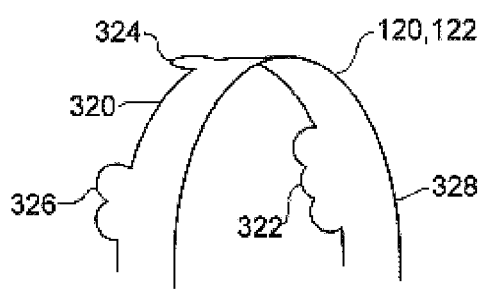

FIG. 8C illustrates another embodiment of a tissue marker in which tissue marking extensions 322, 324, and 326 are asymmetrically arranged on a trailing edge 320 of the cutting loop 122. If an external radio frequency energy source is used to energize the cutting loop 122, a cutting current or sinusoidal waveform can be used to sever tissue at a leading edge 328 of the cutting loop 122. When electrical current passes through the extensions, e.g., as a result of the electrical communication between the extensions 322, 324 and 326 and the cutting loop 122, the enlarged surface areas of extensions 322, 324 and 326 would create a cautery effect resulting in charring or blackening of the surface of the severed tissue in contact with the extensions 322, 324 and 326. The extensions 322, 324 and 326 can be arranged in any pattern or number along the cutting loop 122 to asymmetrically blacken or char the surface of the severed tissue. The extensions 322, 324 and 326 and the cutting loop 122 may be formed as a single piece, or may be formed separately and later attached to each other. The extensions 322, 324 and 326 may comprise a metallic material such as a metal, a metal alloy, a metal laminate, or a metal composite.

Figure 8D:
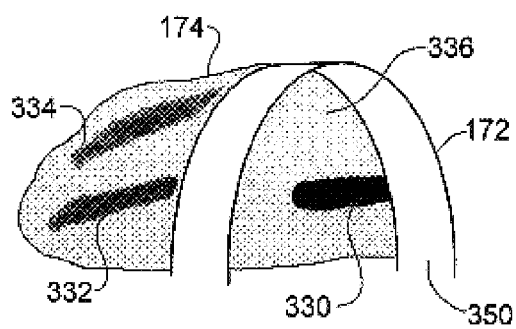

FIG. 8D illustrates yet a further embodiment of the tissue marker in which the collection bag 174 is attached to the collection loop 172. Dyes of different colors 330, 332 and 334 are present on individual regions on an interior surface 336 of the collection bag 174. For example, dye 330 may be red, dye 332 may be blue and dye 334 may be yellow. Although not preferred, the dyes may additionally or alternatively be attached to and extending from the collection loop 172 (not shown). As the severed tissue enters the collection bag 174, the different colored dyes 330, 332 and 334 may contact and mark the severed tissue at different locations.

Figure 8E:
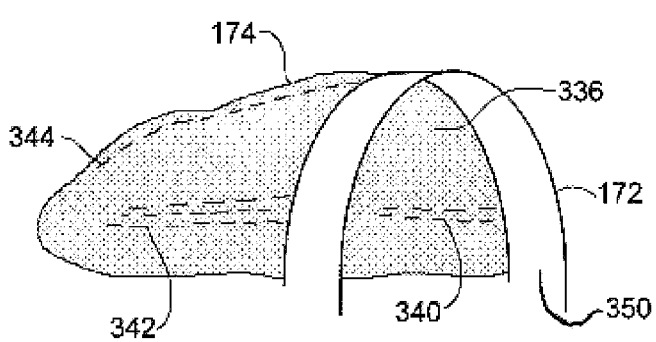

Alternatively, as shown in FIG. 8E, one or more dye colors may be used in different patterns 340, 342 and 344 on the interior surface 336 of the collection bag 174. As yet another alternative (not shown), any combination of colored dye(s), size(s), and/or pattern(s) may be used to coat the interior surface 336 of the collection bag 174. As a further alternative (not shown), the tissue marker may be coated or otherwise disposed inside of a collection bag opening 350 to thereby mark the severed tissue as it passes through the collection bag opening 350. As yet a further alternative (also not shown), the tissue marker may coat the trailing edge of the cutting tool 120, thereby marking the tissue just as it is severed by the leading edge of the cutting tool 120. The dyes may be any suitable dye such as methylene blue, lymphazurine blue and congo red that are commonly used in clinical medicine.

FIG. 9 illustrates an exemplary handle 190 that may be provided to facilitate ease of manipulation of any tissue severing device described herein. The handle 190 is typically provided at the proximal region of the guide or the tubular shaft (not shown) of the tissue severing device. As shown, the handle 190 includes controls 191, 192, 193, 194 that provide control of, for example, a loop extender, a width adjuster, a distal segment positioning mechanism, and a tissue collector controller, respectively. The handle 190 may also contain a knob or dial to control the extension and retraction of the guide as well as a knob or dial to control the window cover (not shown). As an example, the operator may push a knob that is in continuity with the guide 102 in a proximal direction to extend the guide from the distal end of the tubular shaft and pull the knob in a distal direction to retract the guide. The handle 190 may also provide an interface to the external energy source 195, an external vacuum source 196, and/or an external fluid or gas source 197.

The various exemplary embodiments of the tissue severing device facilitates in severing and removing a mass of tissue such as a lesion from a selected region of a patient's breast. The use of the tissue severing device is preferably performed in relation to the internal anatomy of the breast and more specifically to excise part of a lobe, an entire lobe, or an entire lobe with adjacent tissue. It is to be understood that the tissue severing device may also be used, for example, on any other soft tissue regions, including but not limited to, liver and prostate, and may be used on other areas of a human or on non-human animals.

Figure 10:
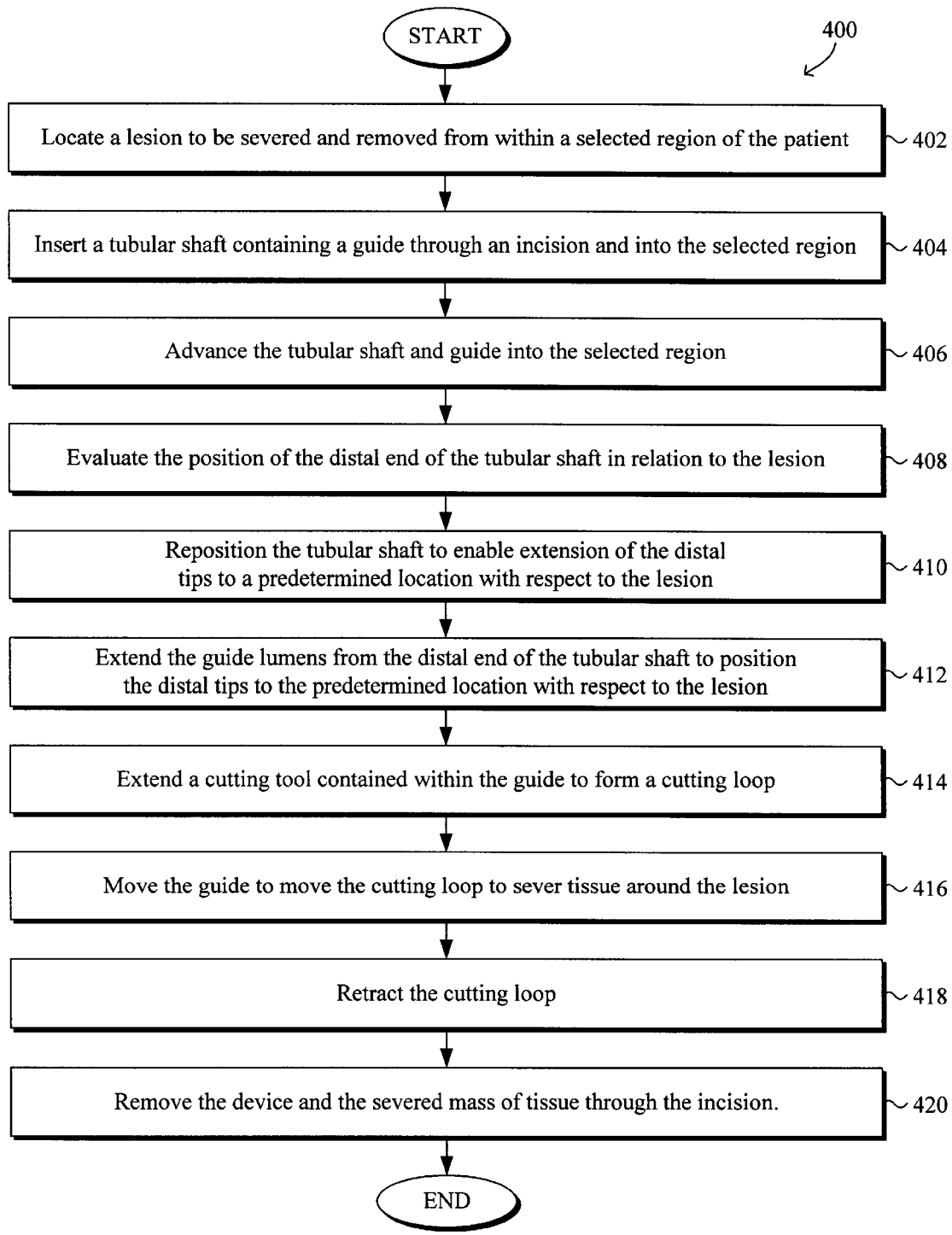
FIG. 10 is a flow chart illustrating a method to severe and remove a mass of tissue or lesion from a patient.

FIG. 10 illustrates a method 400 to sever and remove a mass of tissue or lesion from a patient. At step 402, the lesion to be severed and removed from within a selected region of the patient is located. At step 404, a tubular shaft containing a guide is inserted through an incision and into the selected region.

In one embodiment, the guide is similar to the guide described above with reference to FIG. 1 in which the guide includes two co-linear, co-extensive guide lumens longitudinally extending from a proximal region to a distal terminus along a guide axis, the guide lumens having co-extensive distal segments terminating in distal tips. The guide also includes a cutting tool contained therein and capable of forming a cutting loop extending from the distal tips of the two guide lumens, the cutting loop forming a loop extension axis defined by the direction in which the cutting loop extends. The guide preferably also includes an cutting loop extension control for controlling the degree to which the cutting loop extends from the guide.

In one embodiment, the angle of each distal segment of the guide lumens in relation to the guide axis is generally fixed. Alternatively, the guide lumens have deformable regions immediately proximal to the distal segments that facilitate in changing the direction of the distal segments with respect to the guide axis. In this configuration, the guide includes a distal segment positioning means for varying the direction of each distal segment with respect to the guide axis to thereby adjust the angle between the loop extension axis and the guide axis and selectively position the cutting loop with respect to the guide axis.

In yet another alternative embodiment, a guide comprises a single guide lumen that has a distal segment terminating in a distal tip. The guide also includes a cutting tool that has a fixed end and is at least partially contained within the guide lumen when in a stored configuration and extendible from the distal tip thereof. Extension of the cutting tool from the guide lumen forms a cutting loop having a loop extension axis defined by the direction in which the cutting loop extends. The single lumen guide preferably also includes an cutting loop extension control for controlling the degree to which the cutting loop extends from the guide and a width adjuster for selectively adjust the width of the cutting loop.

At step 406, the tubular shaft and guide are advanced into the selected region. Next, the position of the distal end of the tubular shaft is evaluated in relation to the lesion at step 408. At step 410, the tubular shaft is repositioned by advancing and/or retracting the tubular shaft and/or by changing the angle of insertion to enable extension of the distal tips of the guide lumens to a predetermined location with respect to the lesion. At step 412, the guide lumens are extended from the distal end of the tubular shaft to position the distal tips to the predetermined location with respect to the lesion.

At step 414, a cutting tool contained within the guide is extended from the distal tips of the two guide lumens to form a cutting loop. A loop extension axis is defined by the direction in which the cutting loop extends. At step 416, the guide is moved in order to move the cutting loop along the guide axis severing tissue around the lesion. At step 418, the cutting loop is retracted. Lastly, at step 420, the device and the severed mass of tissue are removed from the selected region through the incision.

The method to sever and remove a mass of tissue may optionally include a number of additional steps. For example, a radiological imaging modality may be used to locate the lesion and visualize all or part of the procedure, including insertion of the device, severing of tissue and/or removal of the severed tissue. Any suitable imaging modality may be used, including but not limited to mammography, including digital and stereotactic mammography, MRI, including three dimensional MRI, and ultrasound, including three-dimensional ultrasound, radial or axial ductal ultrasound. Preferably, ultrasound or three-dimensional ultrasound is used as such imaging modalities render real-time or near real-time images.

According to a preferred embodiment, the cutting tool may be operatively connected to an external energy source. The cutting tool may be energized before and/or during advancement of the guide and the tubular shaft into the selected region such as in step 406 to aid in tissue penetration. The cutting tool may also be energized before and/or during its extension to create a cutting loop in step 414, during step 416 and/or during step 418.

The degree to which the cutting loop extends from the guide lumens, the width of the cutting loop, and/or the angle between the loop extension axis and the guide axis may optionally be varied according to the evaluation of the lesion size and the position of the distal tips of the guide lumens in relation to the lesion, after step 412 and prior to step 414.

The method to sever and remove a mass of tissue described above has the advantage of positioning a portion of the device with a larger diameter or cross-sectional area near the desired location and then extending and advancing a portion of the device with a smaller diameter or cross-sectional area for more precise and accurate positioning of the cutting tool and optionally the collection bag.

In one embodiment, the severed tissue or specimen may be marked in vivo to aid in specimen orientation once the specimen is removed from the body. Such marking may occur while the tissue is being severed and/or after the tissue is severed. The severed tissue may be collected while the tissue is being severed and/or after the tissue is severed. Tissue collection may be accomplished, for example, by extending a collection bag from the guide or from the tubular shaft.

It should be noted that other methods for removing a lesion from a patient may be implemented using different guides, cutting tool arrangements and/or different tubular shafts. In an embodiment utilizing a different tubular shaft, for example, a window may be provided near the distal end of the tubular shaft. The distal tips of the guide lumens are aligned with the window allowing the cutting tool to extend and retract through the window. In this embodiment, after the tubular shaft is inserted through a skin incision, the tissue is penetrated with the tubular shaft until the distal end is proximate to the lesion. To aid in tissue penetration, the distal end of the tubular shaft is preferably configured to a sharp point, trocar or scalpel-like blade. In addition, the distal end may additionally or alternatively be energized by an external energy source. The cutting tool is extended from the distal tips of the guide lumens and through the window to create a cutting loop. The tubular shaft is moved along the direction of the guide axis to allow the cutting loop to sever tissue around the lesion. The cutting tool is retracted and the severed tissue containing the lesion is removed from the patient.

In another embodiment, a tubular shaft having a window near the distal end contains a guide. The guide comprises a guide lumen longitudinally extending from a proximal region to a distal terminus along a guide axis. The guide lumen has a distal segment terminating in a distal tip aligned with the window. After the tubular shaft and guide are advanced into the selected region to position the distal tip of the guide proximate to the lesion, a cutting tool having a fixed end and contained at least partially within the guide lumen is extended from the distal tip of the guide and through the window of the tubular shaft to form a cutting loop. The tubular shaft is used to move the cutting loop along the guide axis to sever tissue around the lesion.

In yet another embodiment, the guide is not housed in a tubular shaft. The guide comprises two co-linear, co-extensive guide lumens longitudinally extending from a proximal region to a distal terminus along a guide axis and the guide lumens have co-extensive distal segments terminating in distal tips. Once the guide is advanced into the selected region to position the distal terminus of the guide proximate to the lesion, a cutting tool contained within the guide is extended from the distal tips of the two guide lumens to form a cutting loop. The guide is then used to move the cutting loop along the guide axis to sever tissue around the lesion and the severed tissue containing the lesion is removed from the selected region.

Figure 11A:
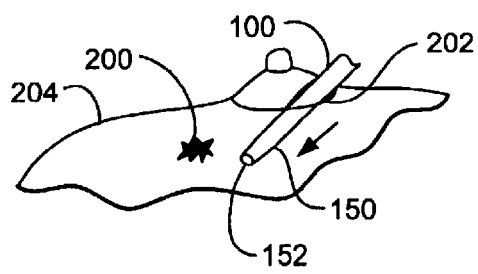
FIGS. 11A–11F, collectively referred to as FIG. 11, illustrate a method in which the device of FIG. 1 is used to remove a lesion from a human breast.
Figure 11B:
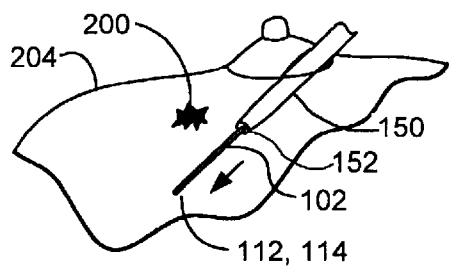

Although the inventive device may be employed for severing a mass of tissue containing a lesion from any soft tissue site, one preferred use of the device is to excise a lesion from breast tissue. FIG. 11 illustrates the removal a lesion from within a selected region of a patient's breast utilizing one embodiment of the device described above with reference to FIG. 1. FIG. 11A illustrates the insertion of device 100 through an incision 202 located at the periareolar region of the breast 204. Once the distal end 152 of the tubular shaft 150 is positioned proximate to the lesion 200, the distance and angle of the projected extension of the distal tips 112, 114 of the guide 102 in relation to the lesion 200 is evaluated. Depending on this evaluation, the tubular shaft 150 may be repositioned by changing its angle of insertion and/or distance with respect to the lesion 200.

Figure 11C:
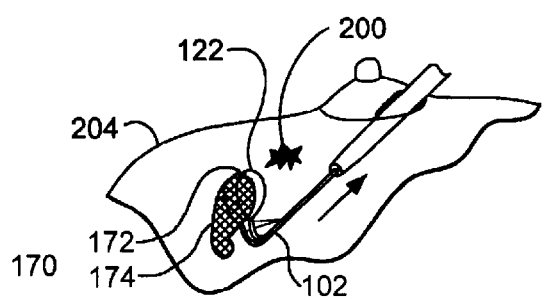

As shown in FIG. 1B, once the tubular shaft 150 is positioned at a desired location, the guide 102, being of smaller diameter than the tubular shaft 150, is advanced from distal end 152 of the tubular shaft 150 to position the distal tips 112, 114 of the guide 102 to a predetermined position distal to the lesion 200. The cutting loop 122 and the tissue collector 170 are then deployed as shown in FIG. 11C. In particular, the tissue collector 170 comprises a tissue collection loop 172 and a tissue collection bag 174.

Figure 11D:
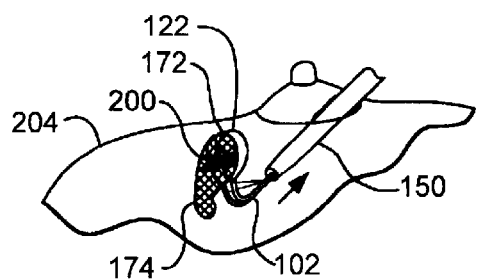
Figure 11E:
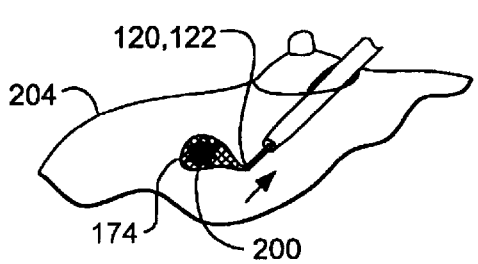

As shown in FIG. 11D, by retracting the guide 102 back into the tubular shaft 150, the cutting loop 122 severs tissue around the lesion 200 while the collection bag 174 collects the severed mass of tissue containing the lesion 200. As the cutting loop 122 is moved proximal to the lesion 200, the cutting loop 122 is retracted followed by retraction of the collection loop 172. As shown in FIG. 11E, retraction of the collection loop 172 closes the opening of the collection bag 174, thereby capturing the severed mass of tissue therein.

Figure 11F:
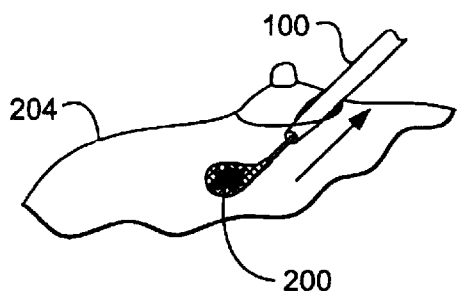

As shown in FIG. 11F, withdrawing the entire device 100 from the breast 204 results in removal of the severed mass of tissue containing the lesion 200 from the breast 204. Optionally, a tissue marker as described above may be employed as well.

Figure 12:
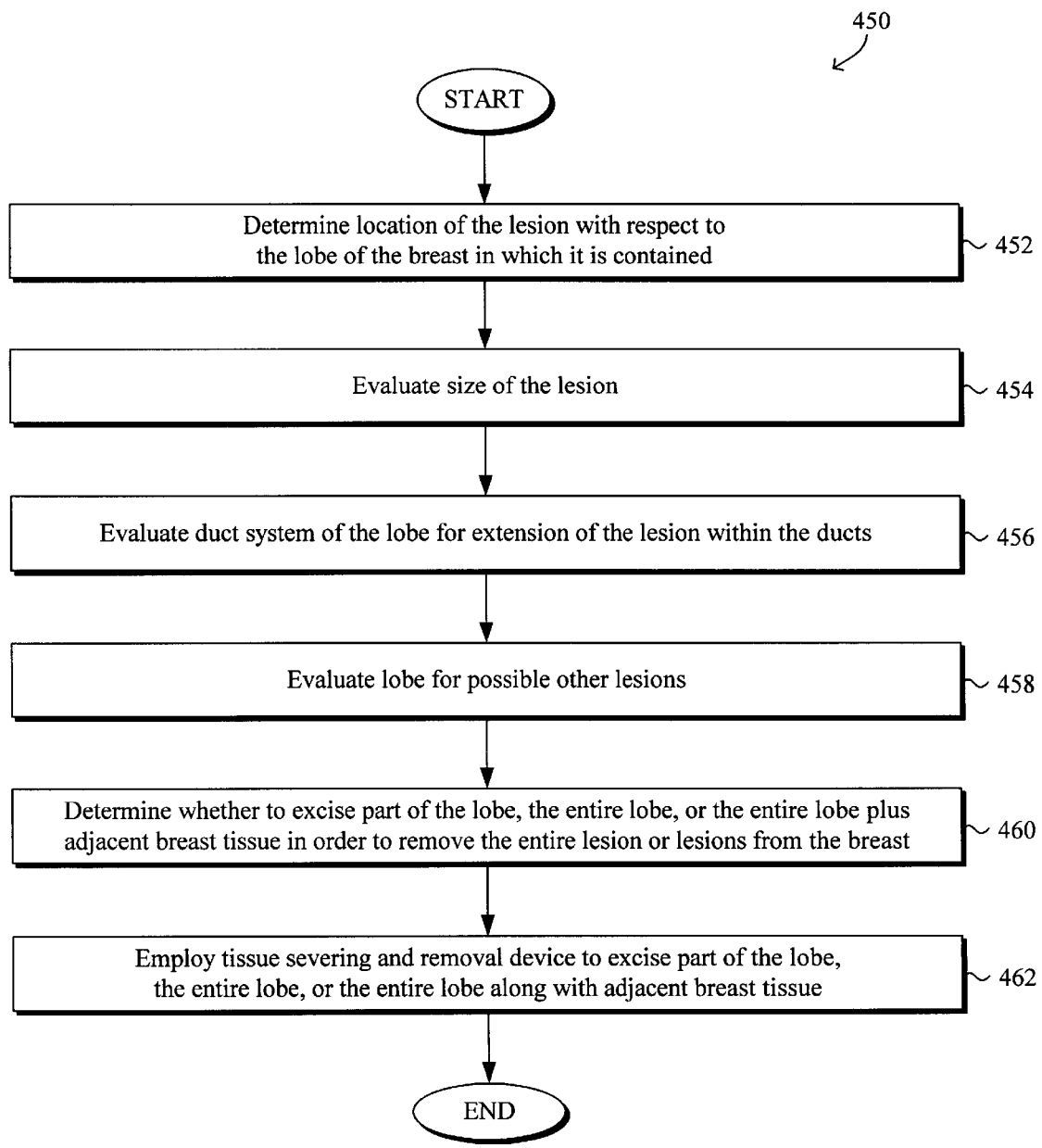
FIG. 12 is a flowchart illustrating a method for removing a lesion performed in relation to the internal anatomy of the breast.

FIG. 12 is a flowchart illustrating a method 450 for removing a lesion performed in relation to the internal anatomy of the breast. The method begins at step 452 in which the location of the lesion is determined with respect to the lobe of the breast in which it is contained. At step 454, the size of the lesion is evaluated. At step 456, the duct system of the lobe is evaluated for extension of the lesion within the ducts. At step 458, the lobe is evaluated for possible other lesions. At step 460, the determination to excise part of the lobe, the entire lobe, or the entire lobe plus adjacent breast tissue in order to remove the entire lesion or lesions from the breast is determined from the determinations made in steps 452–458. Finally, at step 462, a tissue severing and removal device is employed to excise part of the lobe, the entire lobe, or the entire lobe along with adjacent breast tissue.

Unless otherwise specified, the described method involving tissue removal is based on the internal anatomical boundaries of the breast, and more particularly, excision of part of a lobe, an entire lobe or an entire lobe plus adjacent tissue, may be accomplished through surgical tools known in the art or by using the devices as described above.

FIG. 13 illustrates the use of the device of FIG. 1 to perform a breast lobectomy. FIG. 13A illustrates the breast 204 of a human female patient. The lobe 206, located within the breast 204, contains a main duct 208, although breast lobes may often contain more than one main duct. An incision 202 located at a central area of the breast 204 and preferably at the periareolar region is usually made using an additional cutting implement such as a scalpel. The device 100 is inserted through the incision 202 and into the breast 204. As illustrated in FIG. 13B, the guide 102 is advanced from the interior of the tubular shaft 150, adjacent to the lobe 206, to position the distal tips 112, 114 of the guide lumens 104, 106 past the peripheral most aspect of the lobe 206. In addition, FIG. 13B illustrates the deployment of retraction cables 124, 126. As a result, the angle θ between the loop extension axis 123 and the guide axis 107 has been changed from approximately 180° to approximately 90°. As illustrated in FIG. 4, the two guide lumens 104, 106 can be rotated about the guide axis 107 to move the distal tips 112, 114 away from each other in order to widen the cutting loop 122 to allow the cutting loop 122 to encompass the width or diameter of the lobe 206.

Figure 13A:
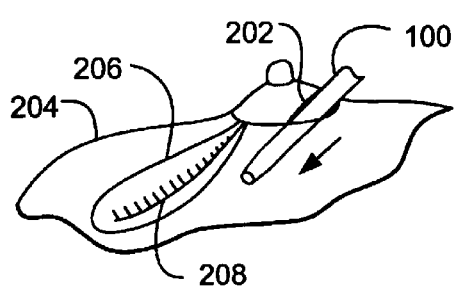
FIGS. 13A–13E, collectively referred to as FIG. 13, illustrate a method in which the device of FIG. 1 is used to perform a breast lobectomy.
Figure 13B:
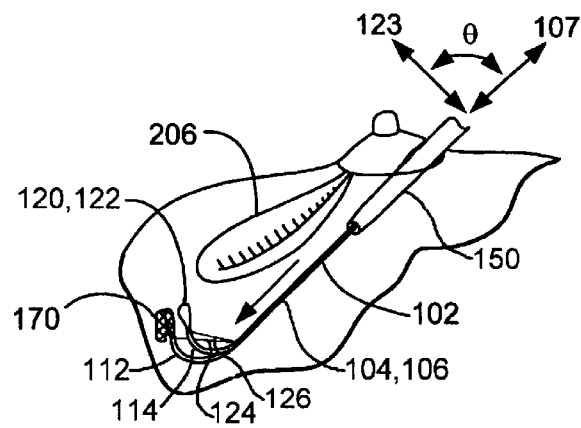
Figure 13C:
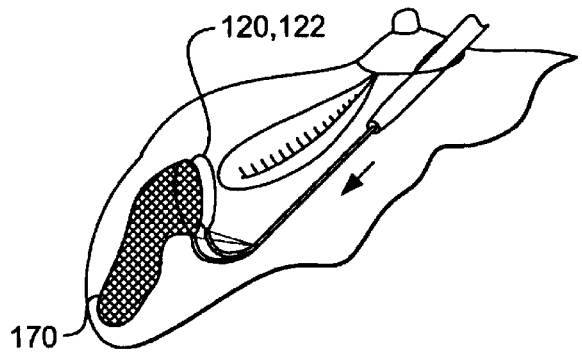

FIG. 13C illustrates extension of the cutting tool 120 to create the cutting loop 122. The tissue collector 170 is deployed either simultaneously with the extension of the cutting tool 120 or preferably after the cutting tool 120 has been extended and slightly moved along the guide axis 107. This keeps the tissue collector 170 at a predetermined distance from the cutting loop 122.

Figure 13D:
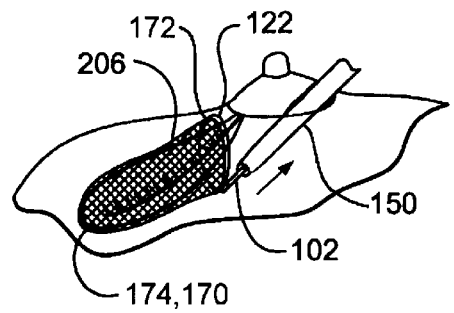
Figure 13E:
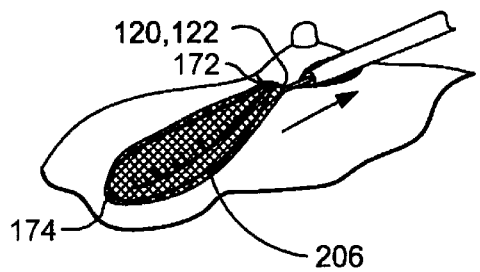

As shown in FIG. 13D, by retracting the guide 102 back into the tubular shaft 150, the cutting loop 122 severs the lobe 206 from surrounding tissue while the collection bag 174 of the tissue collector 170 contains the severed lobe 206. It should be noted that the cutting loop 122 and the collection loop 172 may be adjusted while the guide is retracting to allow the severing action to follow the contour of the lobe 206. As shown in FIG. 13E, once the cutting loop 122 has moved to a predetermined site near the nipple defining the central boundary of the lobe 206, the cutting loop 122 is retracted followed by retraction of the collection loop 172. Retraction of the collection loop 172 closes the opening of the collection bag 174, entrapping the severed lobe 206 therein. The severed lobe 206 may be removed from the breast 204 by withdrawing the entire device 100 through the incision 202 and out of the breast 204 (not shown).

It is to be understood that various other features may be provided in the tissue severing device. For example, locking mechanisms may be provided to ensure a greater degree of control over the spatial relationship between the cutting tool and the guide. In addition, the device may be manually, automatically, and/or remotely controlled. In addition, while use of the inventive methods and devices has generally been described in terms of surgery on the female human breast, the inventive devices and methods may be used on other soft tissue regions, including but not limited to liver and prostate, may be used on other areas of a human or on non-human animals as well.

All patents, patent applications, and publications referenced herein are hereby incorporated by reference in their entireties.

While the preferred embodiments of the present invention are described and illustrated herein, it will be appreciated that they are merely illustrative and that modifications can be made to these embodiments without departing from the spirit and scope of the invention. Thus, the invention is intended to be defined only in terms of the following claims.

What is claimed is:

1. A tissue severing device, comprising:
  a guide comprising two co-linear, co-extensive guide lumens longitudinally extending from a proximal region to a distal terminus along a guide axis, wherein the guide lumens have co-extensive distal segments terminating in distal tips and deformable regions immediately proximal to the distal segments, said deformable regions facilitate in changing the direction of the distal segments with respect to the guide axis;
  a cutting tool contained within the guide and capable of forming a cutting loop extending from the distal tips of the two guide lumens, said cutting loop having a loop extension axis defined by the direction in which the cutting loop extends;
  an extension means for controlling the degree to which the cutting loop extends from the guide; and
  a distal segment positioning means for varying the direction of each distal segment with respect to the guide axis to thereby adjust the angle between the loop extension axis and the guide axis and selectively position the cutting loop with respect to the guide axis.

2. The device of claim 1, further comprising a width adjuster to facilitate in selectively moving the distal tips of the distal segments relative to each other to thereby selectively adjust the width of the cutting loop.

3. The device of claim 2, wherein the width adjuster moves the distal tips of the distal segments and varies the distance between the distal tips by rotating at least one of the guide lumens.

4. The device of claim 3, further comprising a handle at the proximal region of the guide, said handle comprising the extension means and the width adjuster.

5. The device of claim 1, wherein said distal tips are at a generally fixed distance therebetween.

6. The device of claim 1, wherein said distal segment positioning means comprises retraction cables, each attached to one of said distal segments, whereby selective tightening and relaxing of said retraction cables adjusts the direction of the distal segments with respect to the guide axis.

7. The device of claim 6, wherein selective tightening and relaxing of said retraction cables further positions the cutting loop when extended so as to adjust the angle between the loop extension axis and the guide axis to thereby reposition the cutting loop with respect to the guide axis.

8. The device of claim 6, wherein said retraction cables are at least partially and movably disposed within said guide lumens.

9. The device of claim 1, wherein said deformable regions comprise a shape-memory material.

10. The device of claim 1, wherein the angles between each distal segment and the guide axis are one of the same and different.

11. The device of claim 1, wherein the cutting tool comprises an electrically conductive material.

12. The device of claim 11, wherein the electrically conductive material is a metallic material selected from the group consisting of a metal, a metal alloy, a metal laminate, and a metal composite.

13. The device of claim 12, wherein the metallic material is one of titanium, titanium alloy, nickel-titanium alloy, nickel-chromium, and iron-chromium alloy.

14. The device of claim 11, wherein the cutting tool is operatively coupled to an energy source.

15. The device of claim 14, wherein the energy source is one of a heat source, a radio frequency energy source, and an ultrasonic energy source.

16. The device of claim 14, wherein the energy source is a radio frequency energy source and the cutting tool is a component of a monopolar or a bipolar system.

17. The device of claim 1, wherein the cutting tool has a predetermined cross-sectional shape.

18. The device of claim 1, wherein the cutting tool has a cutting edge and a trailing edge.

19. The device of claim 18, wherein the cutting edge is at least one of sharpened and serrated.

20. The device of claim 18, further comprising a vibration-providing means for inducing mechanical vibration of the cutting tool.

21. The device of claim 1, wherein the guide lumens comprise an electrically insulating material.

22. The device of claims 1, further comprising a tissue collector for collecting and removing tissue severed by the cutting tool.

23. The device of claim 22, further comprising a tissue collector controller for controlling said tissue collector.

24. The device of claim 22, wherein the tissue collector is adapted to collect tissue at least one of as the tissue is being severed and after the tissue is severed.

25. The device of claim 22, wherein the tissue collector comprises a tissue collection bag, said collection bag being one of directly and indirectly attached to the distal terminus of the guide.

26. The device of claim 25, further comprising means for opening and closing the tissue collection bag.

27. The device of claim 25, wherein said tissue collection bag is attached to said cutting tool whereby increasing and decreasing the size of said cutting loop opens and closes said tissue collection bag, respectively.

28. The device of claim 25, wherein said tissue collection bag is electrically insulated from said cutting tool.

29. The device of claim 25, wherein said collection bag is deployable and adjustable independent of said cutting tool and wherein said tissue collector further comprises a collection loop adapted to be selectively opened and closed.

30. The device of claim 25, wherein said tissue collector further comprises a tissue collection loop adapted to be selectively opened and closed and two tissue collection lumens having collection distal tips from which said collection loop extends, said tissue collection bag being attached to said tissue collection loop.

31. The device of claim 30, wherein said collection loop is aligned with said cutting loop.

32. The device of claim 25, wherein the collection bag comprises an impermeable material.

33. The device of claim 32, wherein the impermeable material is selected from the group consisting of polyethylene, polypropylene, polybutylene, polyamide, polyimide, polyester, polyvinyl chloride, polyvinyl fluoride, polyvinylidene fluoride, polycarbonate, and polytetrafluoroethylene.

34. The device of claim 1, further comprising a tissue marker, said tissue marker configured to mark tissue severed by the cutting tool.

35. The device of claim 34, wherein the tissue marker is in electrical communication with an external energy source.

36. The device of claim 35, wherein the external energy source is a radio frequency energy source.

37. The device of claim 36, wherein the tissue marker comprises means for charring or creating blackened marks on the surface of the severed tissue.

38. The device of claim 37, wherein the tissue marker comprises marking segments extending from a trailing edge of said cutting loop.

39. The device of claim 38, wherein the marking segments comprise a metallic material.

40. The device of claim 38, wherein the marking segments are asymmetrically arranged along the trailing edge of the cutting loop.

41. The device of claim 38, wherein the marking segments comprise electrically conductive wires.

42. The device of claim 41, wherein at least some of the electrically conductive wires are interwoven to create a pattern asymmetrically arranged along the trailing edge of the cutting loop.

43. The device of claim 38, wherein the marking segments comprise extensions of the cutting loop asymmetrically arranged thereon.

44. The device of claim 34, wherein the tissue marker comprises a dye for staining the severed tissue.

45. The device of claim 44, wherein the dye is located on a plurality of regions on the interior surface of one of a collection bag any, the cutting loop.

46. The device of claim 45, wherein the individual regions of dye are arranged in an asymmetric pattern on the interior surface of one of the collection bag and the cutting loop.

47. The device of claim 44, wherein the collection bag comprises an opening, said opening containing the dye in individual regions thereon.

48. The device of claim 44, wherein said dye is of at least two different colors.

49. The device of claim 1, wherein the guide lumens are affixed to each other.

50. The device of claim 1, wherein the guide lumens are housed in a tubular shaft, said tubular shaft having a distal end and a proximal end.

51. The device of claim 50, wherein the tubular shaft further includes at least one accessory lumen.

52. The device of claim 51, further comprising a tissue collector for collecting and removing tissue severed by the cutting tool, said tissue collector being contained in one of the at least one accessory lumen.

53. The device of claim 52, wherein the tubular shaft has at least one opening at the distal end and wherein the tissue collector is adapted to extend from and retract into the tubular shaft through one of the at least one opening at the distal end.

54. The device of claim 51, wherein the at least one accessory lumen comprises at least one transport lumen that allows a material to be transported therethrough to the distal end.

55. The device of claim 54, further comprising a source of gas, liquid or a combination thereof in fluid communication with the at least one accessory lumen.

56. The device of claim 54, wherein the at least one accessory lumen additionally comprises at least one vacuum lumen operatively connected to a vacuum source.

57. The device of claim 54, wherein the at least one accessory lumen comprises at least one vacuum lumen operatively connected to a vacuum source.

58. The device of claim 50, further comprising a tissue penetration means for facilitating tissue penetration, said tissue penetration means being attached to said distal end of said tubular shaft.

59. The device of claim 58, wherein the tissue penetration means comprises at least one of a sharpened edge and a sharpened tip.

60. The device of claim 58, wherein the tissue penetration means is operatively coupled to an external energy source.

61. The device of claim 60, wherein the external energy source is one of a radio frequency energy source and an ultrasonic energy source.

62. The device of claim 61, wherein the external energy source is the radio frequency energy source and the tissue penetration means is a component of a monopolar or a bipolar system.

63. The device of claim 50, wherein the tubular shaft has at least one opening at the distal end and wherein the guide lumens are adapted to extend from and retract into the tubular shaft through at least one of the at least one opening at the distal end.

64. The device of claim 63, further comprising an extension-retraction controller adapted to extend and retract the guide lumens with respect to the tubular shaft.

* * * * *